United States Patent [19]

Robert et al.

[11] Patent Number: 4,741,347

[45] Date of Patent: May 3, 1988

[54] PIEZOELECTRIC CURRENT GENERATING DEVICE

[75] Inventors: Hervé Robert, Paris; Henry Kogan, 15 rue du Bac, 75007 Paris, both of France

[73] Assignee: Henry Kogan, Paris, France

[21] Appl. No.: 873,578

[22] Filed: Jun. 12, 1986

[30] Foreign Application Priority Data

Nov. 22, 1985 [FR] France .................................. 85 17314

[51] Int. Cl.$^4$ ............................................. A61N 1/32
[52] U.S. Cl. ................................................... 128/800
[58] Field of Search ........... 128/783, 800, 801, 419 R, 128/419 D, 741; 310/339; 361/232

[56] References Cited

U.S. PATENT DOCUMENTS 3,389,275  6/1968  Brothers ........................ 310/339 X
4,099,519  7/1978  Warren ............................... 128/741

FOREIGN PATENT DOCUMENTS 3121254  12/1982  Fed. Rep. of Germany ...... 310/339
  65169   1/1956  France ................................ 128/783
2500745   9/1982  France ................................ 128/800
85/05042 11/1985  PCT Int'l Appl. ................. 128/800
1448644   9/1976  United Kingdom ................ 128/800
2128093   4/1984  United Kingdom ............ 128/419 R Primary Examiner—Lee S. Cohen
Attorney, Agent, or Firm—Ralph H. Dougherty

[57] ABSTRACT

In an electric pulses generating apparatus for therapeutic applications, a piezoelectric generator is connected to electrodes. Some of the electrodes at least are placed in contact or in vicinity of a skin of a patient to be treated. A current of piezoelectric origin in caused to flow through a distribution head formed with notches.

13 Claims, 3 Drawing Sheets

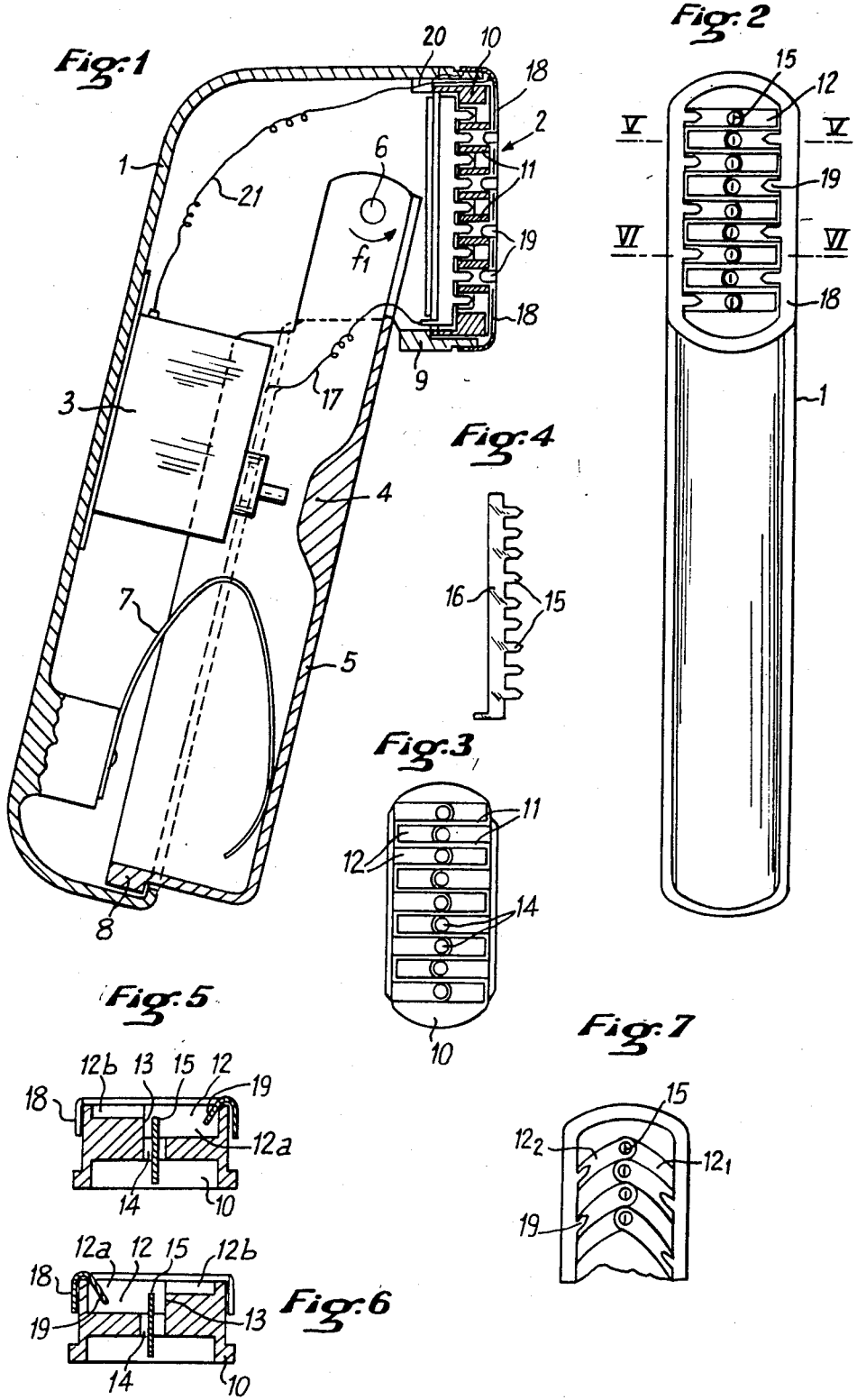

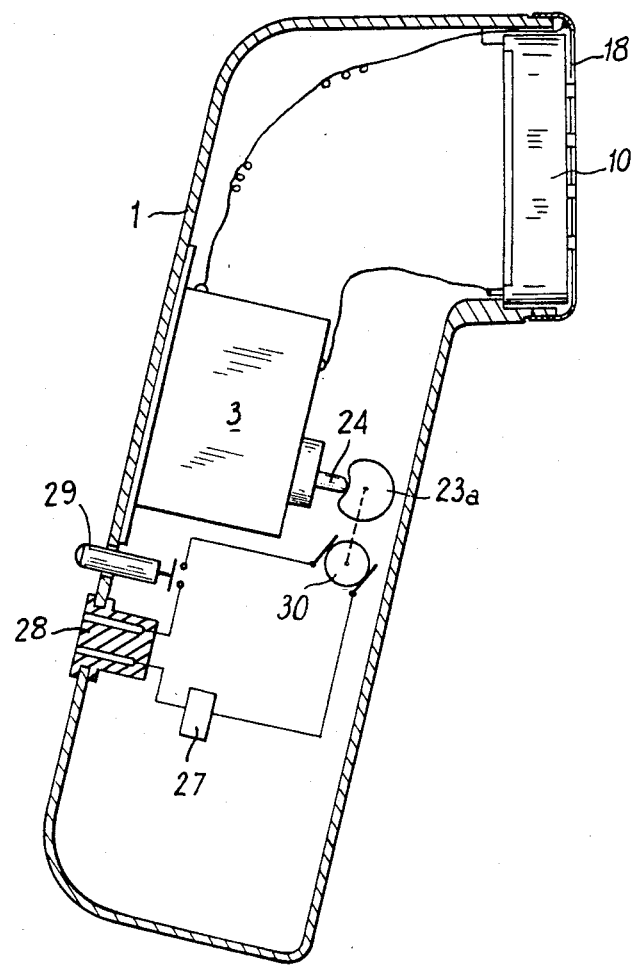

PIEZOELECTRIC CURRENT GENERATING DEVICE

FIELD OF THE INVENTION

The present invention generally relates to piezoelectric current generating devices which are used for various treatments in which it appears useful that high voltage discharges or glow discharges are caused to flow through some portions of the body of a patient.

BACKGROUND OF THE INVENTION

Apparatus of this type are used particularly for treatment of muscular pains and include electrodes between which flows a current of piezoelectric origin.

Piezoelectric generators are also used in fields of application other than the therapeutical fields and, in particular, they are used as igniters of various devices due to their great operational security.

There is in this respect particular by known gas lighter devices which comprise in a body of plastics material a piezoelectric generator having a terminal connected to an electrode while an other terminal is connected to a conductive nipple forming, with the electrode, an air gap in which flashes a spark when the piezoelectric generator is energized.

BRIEF SUMMARY OF THE INVENTION

This invention relates to improvements for improving the operation of apparatus, particularly apparatus made as the hereabove gas lighter devices, but enabling to control the flow of the glow discharges and electric sparks as a function of the therapy which is applied.

This invention provides also improvements enabling, as the case may be, to motorize the apparatus which produces glow discharges or electrical sparks at a chosen rate without having to resort to other operations except maintaining a pressure on a switch.

According to the invention, the electric impulse generating apparatus for therapeutic application, in which a piezoelectric generator is connected to electrodes of which some at least are placed in contact or in vicinity of a skin of a patient to be treated, is characterized in that a current of piezoelectric origin is caused to flow through a distribution head formed with notches.

Various other features of the invention will become more apparent from the hereafter detailed description.

BRIEF DESCRIPTION OF THE DRAWINGS

Embodiments of the invention are shown, by way of non limiting examples, in the accompanying drawings, wherein:

FIG. 1 is a longitudinal elevation sectional view of an electric treatment device of this invention;

FIG. 2 is a front elevation view of the device;

FIG. 3 is a front elevation view of the distribution head of a preferred embodiment of this invention;

FIG. 4 is a side elevation view of an electrode which is part of the device;

FIGS. 5 and 6 are sectional view respectively taken along lines V—V and VI—VI of FIG. 2;

FIG. 7 is an elevation view similar to FIG. 3 of the distribution head of a variant;

FIG. 9 is a view similar to that of FIG. 8, but showing still another embodiment.

DETAILED DESCRIPTION OF THE INVENTION

Figure 8:
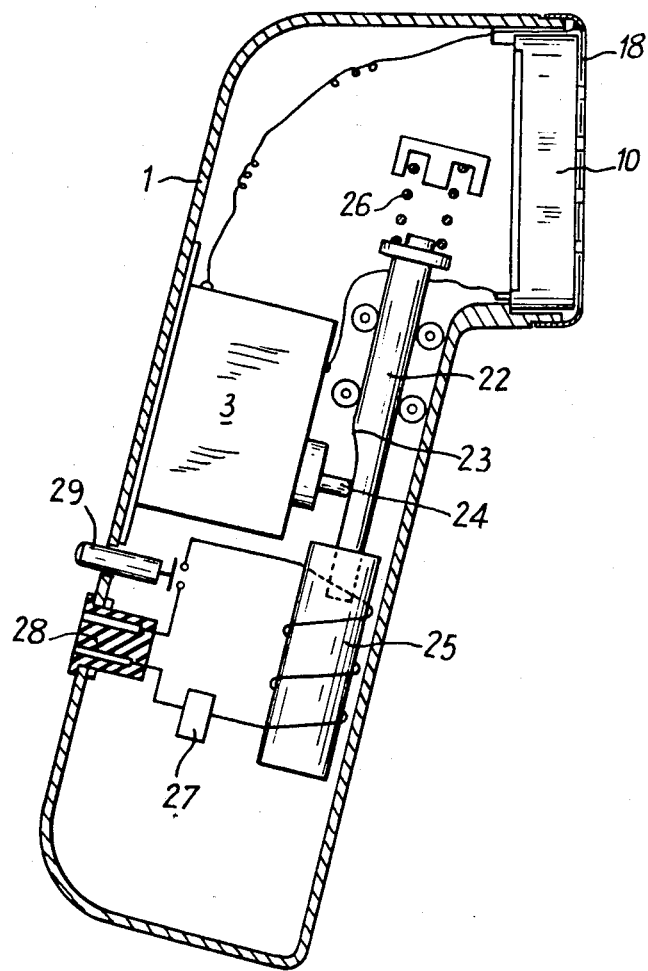
FIG. 8 is a view similar to FIG. 1 of another embodiment.

The device shown in the drawings comprises a body 1 of any suitable shape, preferably designed for having ergonomic qualities, particularly in order to be easily maintained in hand of a user when the user wishes to present a distribution head 2, which is described hereafter, on a portion of his body to be treated.

The body 1 of the device is hollow and contains a piezoelectric generator 3 which can be operated by a boss 4 of a handle or pedal 5 through pressure exerted by the user on the handle or pedal 5.

FIG. 1 shows that the handle 5 is articulated for example on a pin 6.

It is advantageous that the body 1 and handle 5 are made of a synthetic material, since in that case their manufacture is made easy, particularly by molding.

A spring 7 is fixed inside an abutment 8 in order to bear against the inner face of the handle 5 with a tendency to pivot the handle 5 in direction of an arrow $f_1$.

An abutment 8 limits amplitude of the motion which can be made by the handle 5.

As shown in FIG. 1, the body 1 is formed at one end with an opening 9 in which is inserted and maintained the distribution and treatment head 2.

The treatment head 2 comprises a grid 10 (FIG. 3) in an insulating material, for example a plastics material. The face of the grid 10 which is directed outwardly is formed with transverse walls 11 separating successive notches 12 having alternately a deep portion 12a and a shallow portion 12b.

FIGS. 5 and 6 are sectional views of two successive notches 12, and as shown the deep portion 12a and the shallow portion 12b are separated by a shoulder 13 at the foot of which is formed an opening 14 in the bottom of each notch.

The openings 14 are used for passage of electrodes 15 extending from a small bar 16 (FIG. 4) fixed below the grid 10 and connected by a lead 17 (FIG. 1) to one of the poles of the piezoelectric generator 3.

It is advantageous, as shown in the drawings, that the grid 10 be engaged with a slip fit in the opening 9 so that it can be possibly changed as a function of the treatment to be carried out.

The grid 10 is maintained inside the opening 9 of the body 1 by a belt 18 made of a conductive material, for example a metal, which is fitted onto the body 1 and fixed to the body 1 either by a clipping arrangement or by simple friction in order also to allow, if so desired, the belt 18 to be changed.

The belt 18 comprises studs or contacts 19 which are provided in order to protrude into the notches 12, either in the deep portion of the notches 12, as shown, or in the shallow portion by simply turning the belt 18 over.

A contact 20 is provided in the thickness of the body 1 for electrically connecting the belt 18 with the second pole of the piezoelectric generator 3 by a lead 21.

FIG. 3 shows that the notches 12 can be rectilinear, while FIG. 7 shows that the notches 121, 122 can be arcuate. Possibly, they could also have a zigzag shape according to the type of treatment which it is desired to practice.

FIG. 8 shows a development of this invention in which the piezoelectric generator 3 is no more operated manually by a lever or a knob, but by means of a mobile element 22 which is electrically operated.

In the example as shown, the mobile element forms a cam 23 actuating a pusher element 24 of the piezoelectric generator 3.

The element 22 forms on the other hand the core of an electromagnet 25 with a plunger. It is advantageous that the element 22 is connected to a spring 26 used for bringing it back to its starting portion after each impulse caused by the electromagnet 25. Supplying of current to the electromagnet 25 is advantageously controlled by a time delay circuit 27.

In the embodiment of FIG. 8, the only thing an user has to do is, once he has set in position an electric lead in a socket 28, to act on a switch 29 closing a circuit of the electromagnet 25 so that an operative frequency of the electromagnet 25 depends thereafter only on the time delay unit 27.

Of course, the hereabove described device can be replaced, if one wishes so, by a rotating electric motor.

In FIG. 9, the mobile element operating the piezoelectric generator 3 is a rotating electric motor diagrammatically shown at 30 and mechanically connected to a cam 23a actuating the pusher member 24 in the very same manner as in FIG. 8 for the cam of the mobile element 22. The rotating electric motor 30 is advantageously controlled in the same manner through the time delay 27 by the switch 29, an electric lead being set in position in the socket 28.

The drawings show that the walls 11 of the grid 10 are protruding with respect to the electrodes 15 which are therefore at a lower level than that of the upper edge of the walls 11 and of the most protruding portion of the conducting belt 18. In this way, the skin of a patient to be treated cannot come in direct contact with the electrodes 15, and the result is that the glow discharges and sparks are always produced even when the patient skin is wet.

The studs or contacts 19 of the conductive belt 18 are shown with an arcuate configuration in FIGS. 5 and 6. One would not depart from the scope of the invention by making them flat or substantially flat, or with any other shape for modifying the path of travel of the glow discharges and sparks, particularly for patients the skin of which is wet or exhibits characteristics such that the glow discharges and/or sparks have to be more or less reinforced.

The invention is not limited to the embodiments shown and described in detail and various modifications thereof can be carried out thereto without departing from its scope as shown in the dependent claims.

What is claimed is :

1. An electric pulse generator apparatus for therapeutic applications on a patient, comprising a body with a distribution head provided with notches and having a peripherally conductive belt, a piezoelectric generator, a plurality of electrodes connected to one pole of said generator, wherein said plurality of electrodes are respectively located in said notches at a level lower than the level of said conductive belt, and wherein said peripherally conductive belt is connected to another pole of said generator, whereby a current of piezoelectric origin is caused to flow through said notches between said plurality of electrodes and said conductive belt of said head.

2. The apparatus as set forth in claim 1, wherein said notches are defined by walls in the distribution head.

3. The apparatus as set forth in claim 2, wherein said plurality of electrodes are at a level inferior than that of an upper edge of the walls, whereby sparks are produced even when said walls are in contact with a wet skin.

4. The apparatus as set forth in claim 1, wherein said belt has studs or contacts protruding into some at least of the notches.

5. The apparatus as set forth in claim 4, wherein said studs or contacts of said conductive belt have a curvature which is a function of the flow of current.

6. The apparatus as set forth in claim 1, wherein each of said notches comprises a deep portion and a shallow portion for defining a shoulder, with one of said plurality of electrodes being placed in the vicinity of said shoulder.

7. The apparatus as set forth in claim 6, wherein said belt forms a removable cover having studs or contacts which are indifferently engaged in the deep portion and in the shallow portion of said notches.

8. The apparatus set forth in claim 1, wherein said distribution head is removably mounted in said body to be interchangeable.

9. The apparatus as set forth in claim 1 wherein said notches are rectilinear.

10. The apparatus as set forth in claim 1, wherein said notches are arcuate.

11. The apparatus as set forth in claim 1, wherein said body comprises a mobile element and wherein said generator includes an actuator element operatively connected to said mobile element.

12. The apparatus as set forth in claim 11, further comprising an electromagnet, the core of which is said mobile element.

13. The apparatus as set forth in claim 11, further comprising a rotating motor operatively connected to said mobile element.

* * * * *

UNITED STATES PATENT AND TRADEMARK OFFICE
CERTIFICATE OF CORRECTION

PATENT NO. : 4,741,347

DATED : May 3, 1988

INVENTOR(S) : Herve' Robert and Henry Kogan

It is certified that error appears in the above-identified patent and that said Letters Patent is hereby corrected as shown below:

In Column 3, Line 7, change "portion", to -- position --.

Signed and Sealed this

Eighteenth Day of October, 1988

Attest:

DONALD J. QUIGG

Attesting Officer

Commissioner of Patents and Trademarks